US008571180B2

(12) United States Patent
Hörnig et al.

(10) Patent No.: US 8,571,180 B2
(45) Date of Patent: Oct. 29, 2013

(54) MINIATURE X-RAY TUBE FOR A CATHETER

(75) Inventors: Mathias Hörnig, Erlangen (DE); Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 474 days.

(21) Appl. No.: 12/900,525

(22) Filed: Oct. 8, 2010

(65) Prior Publication Data

US 2011/0087062 A1 Apr. 14, 2011

(30) Foreign Application Priority Data

Oct. 13, 2009 (DE) ........................ 10 2009 049 182

(51) Int. Cl.
*A61N 5/10* (2006.01)
*H01J 35/02* (2006.01)

(52) U.S. Cl.
USPC ................ 378/122; 600/3; 377/742; 377/904

(58) Field of Classification Search
None
See application file for complete search history.

(56) References Cited

U.S. PATENT DOCUMENTS

| | | | | |
|---|---|---|---|---|
| 6,553,096 | B1 | 4/2003 | Lu | |
| 6,718,012 | B2 | 4/2004 | Ein-Gal | |
| 7,359,484 | B2 | 4/2008 | Lu | |
| 2001/0009970 | A1* | 7/2001 | Chornenky et al. | 600/3 |
| 2002/0063500 | A1* | 5/2002 | Keren | 313/30 |
| 2003/0002627 | A1* | 1/2003 | Espinosa et al. | 378/136 |
| 2005/0031083 | A1* | 2/2005 | Kindlein | 378/136 |

FOREIGN PATENT DOCUMENTS

| | | | |
|---|---|---|---|
| DE | 19829444 | A1 | 1/2000 |
| DE | 19829447 | A1 | 1/2000 |
| DE | 60311440 | T2 | 8/2007 |
| EP | 0998748 | B1 | 10/2005 |
| WO | WO 9707740 | A1 | 3/1997 |
| WO | WO 2004110111 | A2 | 12/2004 |

OTHER PUBLICATIONS

Xoft, Inc.; Axxess with Axxent Innovative technology for the practice of radiation oncology; Prospekt: MS-0014 Rev. D 7/08; 2008.
Xintek, Inc. Nanotechnology Innovations, Xintek's Field Emission X-Ray Technology.

* cited by examiner

*Primary Examiner* — Hoon Song
*Assistant Examiner* — Danielle Fox

(57) ABSTRACT

A miniature X-ray tube for intravascular or intracorporeal radiation treatment in living beings is proposed. The X-ray tube comprises a cylindrical housing section with a longitudinal axis. The miniature X-ray tube also comprises a cylindrical or cylindrical-tube-shaped first field emission cathode arranged concentrically about the longitudinal axis in the housing with a plurality of carbon nanotubes which emit electrons radially outward. The miniature X-ray tube also comprises a second field emission cathode in the housing with a plurality of carbon nanotubes which emit electrons in the direction of longitudinal axis. The miniature X-ray tube only emits little heat and is robust against mechanical stresses.

18 Claims, 2 Drawing Sheets

MINIATURE X-RAY TUBE FOR A CATHETER

CROSS REFERENCE TO RELATED APPLICATIONS

This application claims priority of German application No. 10 2009 049 182.1 filed Oct. 13, 2009, which is incorporated by reference herein in its entirety.

FIELD OF THE INVENTION

The invention relates to a miniature X-ray tube and a catheter with a miniature X-ray tube.

BACKGROUND OF THE INVENTION

Conventional X-ray tubes substantially comprise a vacuum chamber with a housing enclosing a cathode and an anode. The cathode forms the negative electrode, which emits electrons toward the positive anode. The electrons are attracted from the anode and strongly accelerated by an electrical field between the anode and cathode. The anode is typically made of a metal, for example tungsten, molybdenum or palladium. When the electrons bombard the anode, their energy is for the most part converted into heat. Only a fraction of the kinetic energy can be converted into X-ray photons, which are emitted by the anode in the form of an X-ray beam. The X-ray beam generated in this way exits the vacuum chamber through a radiation-permeable window made of a material with a low atomic number.

Applications in industrial and medical imaging and for therapeutic treatment are nowadays unimaginable without X-ray devices. X-ray devices are also used to treat vascular diseases inside patients' bodies. For this, X-ray devices must be miniaturized sufficiently to enable them to be introduced into a patient's vessels.

An X-ray tube of this kind is disclosed in DE 198 29 444 A1. The X-ray device is preferably arranged at the distal end of a catheter. The X-ray tube has a vacuum housing equipped with a cylindrical housing section the inside wall of which is coated with a target material. A cylindrical isocentrically arranged field emission cathode extending along the longitudinal axis is located in the vacuum housing and emits electrons radially outward in the direction of the target material for the generation of X-rays. When the electrons hit the target material, X-rays are generated which penetrate the vacuum housing. The X-ray tube can be designed small enough to enable the treatment of even coronary vessels.

For some time now, carbon nanotubes have also been used to build cathodes for multi-beam X-ray tubes. For example, PCT application WO 2004/110111 A2 discloses an X-ray tube of this kind. The multi-beam X-ray tube comprises a stationary field emission cathode and an anode facing the cathode. The cathode comprises a plurality of stationary, individually controllable electron-emitting carbon nanotubes disposed in a predetermined pattern on the cathode. The anode comprises a plurality of focal points disposed in a predetermined pattern corresponding to the pattern of the carbon nanotubes. A vacuum chamber encloses the anode and cathode.

The solution disclosed in WO 2004/110111 A2 offers many advantages compared to conventional thermionic sources of X-radiation. It eliminates the anode's heating element, operates at room temperature, generates pulsed X-rays with a high repetition rate and generates a plurality of beams with different focal points.

SUMMARY OF THE INVENTION

The object of the invention is to utilize the advantages of cathodes with carbon nanotubes with miniaturized X-ray devices and to disclose an improved miniature X-ray device for a catheter.

According to the invention, the object is achieved with the miniature X-ray tube and the catheter described in the claims.

The invention claims a miniature X-ray tube for intravascular or intracorporeal radiation treatment in living beings with a housing comprising a cylindrical housing section with a longitudinal axis. The miniature X-ray tube also comprises a cylindrical or cylindrical-tube-shaped first field emission cathode arranged concentrically about the longitudinal axis in the housing section with a plurality of carbon nanotubes, which emit electrons radially outward, and/or in the housing section a second field emission cathode with a plurality of carbon nanotubes, which emit electrons in the direction of the longitudinal axis. The invention has the advantages that the miniature X-ray tube only emits little heat and is robust against mechanical stresses. In addition, the design is simpler than those known from the prior art. It is also advantageous that it is possible to establish an optimum distance between the first field emission cathode and the housing section (outer sleeve).

In a further embodiment, the carbon nanotubes can be arranged on the internal or external side of the cylindrical-tube-shaped first field emission cathode or on the external side of the cylindrical first field emission cathode. This permits a homogeneous dose distribution of the X-rays.

In a development, a plurality of cylinder rings to which are applied carbon nanotubes form the field emission cathode.

Advantageously, a flexible film can be applied to the carbon nanotubes to form the first field emission cathode.

In addition, the carbon nanotubes can be printed or sputtered onto the flexible film.

In a preferred embodiment, the miniature X-ray tube can comprise at least one tubular-cylinder-shaped anode arranged outside the first field emission cathode concentrically to the longitudinal axis in the housing section.

The invention also claims a catheter with shaft, the distal end of which is provided with a miniature X-ray tube according to the invention. The advantage of this is that it is possible to produce a compact and inexpensive tool for intravascular and intracorporeal radiation treatment of living beings.

BRIEF DESCRIPTION OF THE DRAWINGS

Further special features and advantages of the invention are evident from the following explanation of several exemplary embodiments with reference to schematic drawings, which show.

DETAILED DESCRIPTION OF THE INVENTION

Figure 1:
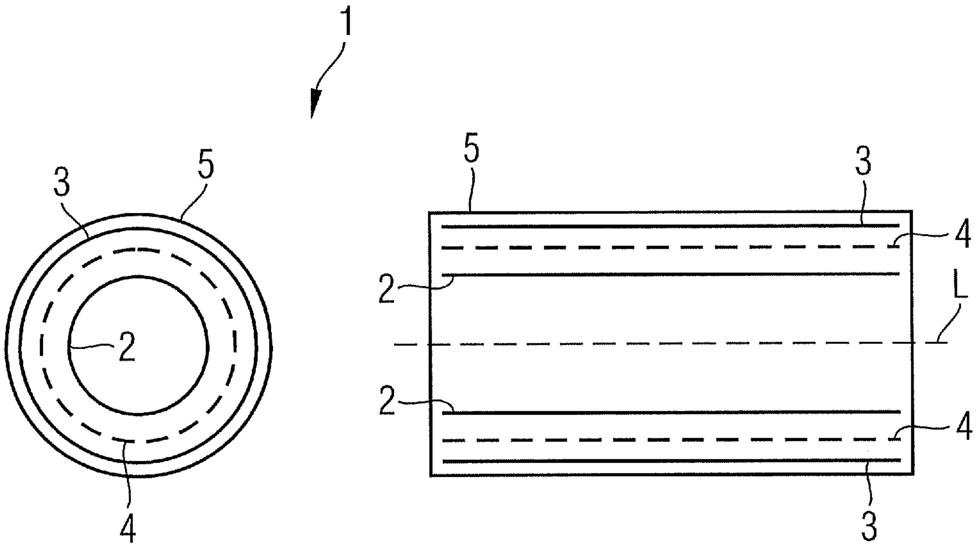
FIG. 1: a miniature X-ray tube with a field emission cathode with carbon nanotubes.

FIG. 1 shows a schematic cross-section and longitudinal section through a miniature X-ray tube 1 according to the invention. In a cylindrical-tube-shaped housing section 5 of the miniature X-ray tube 1 with a longitudinal axis L, a cylindrical or cylindrical-tube-shaped field emission cathode 2 is arranged concentrically. The field emission cathode 2 comprises a plurality of carbon nanotubes (not shown in FIG. 1), which emit electrons in the direction of the housing section 5. The electrodes hit a cylindrical anode 3 arranged concentrically to the longitudinal axis L inside the housing section 5. The electrons are focused onto the anode 3 with the aid of a cylindrical cathode-focusing element 4, for example in the form of a perforated or mesh cylinder arranged concentrically between the field emission cathode 2 and the anode 3. The bombarding electrons generate X-rays emitted radially to the longitudinal axis L. Alternatively, it is also possible for a plurality of transmission anodes to be arranged in series.

Figure 2:
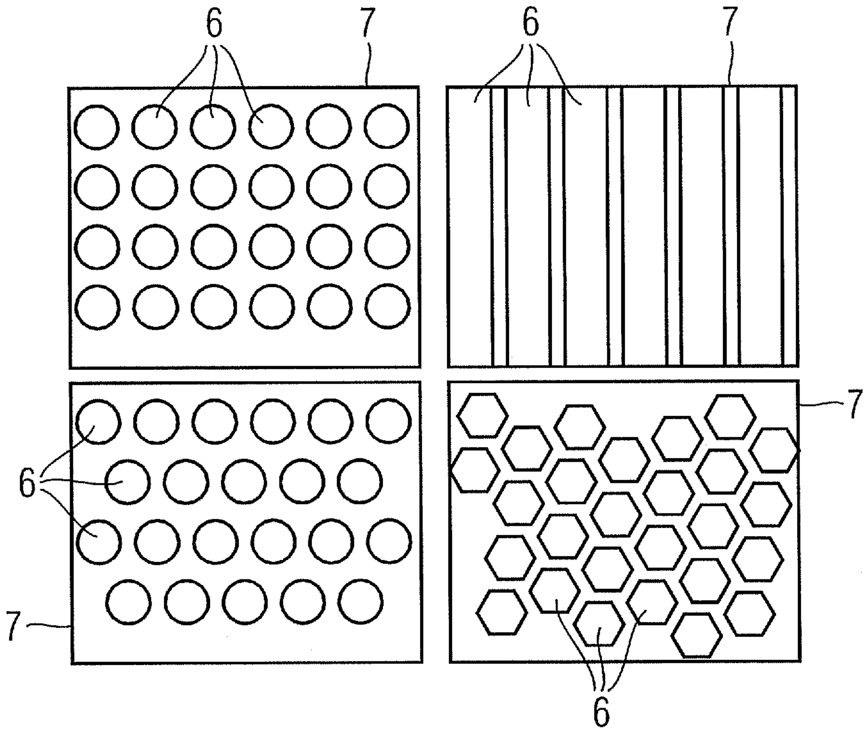
FIG. 2: an arrangement of carbon nanotubes on a flexible carrier.

The carbon nanotubes can, for example, be applied by laser-coating onto the external side of a cylindrical tube serving as a carrier. FIG. 2 shows alternatives to this according to the invention. Carbon nanotubes 6 are applied to a carrier substrate 7, for example to a film. The carbon nanotubes can be printed or sputtered, for example. The flexible carrier substrate 7 can then be simply bent and applied to a cylinder inner side or cylinder outer side serving as a holder. However, the flexible carrier substrate 7 can also be bent into a cylindrical shape without a holder and in this way, inserted into the tip of a catheter, for example.

Figure 3:
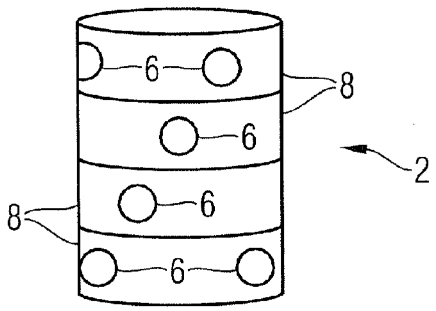
FIG. 3: a field emission cathode made of rings with carbon nanotubes.

FIG. 3 shows a further embodiment of a field emission cathode 2 according to the invention with carbon nanotubes 6. Hereby, the carbon nanotubes 6 are arranged on a plurality of carrier rings 8 or carrier cylinders, which can be introduced into the shaft of a catheter. For example, three carbon nanotubes 6 each offset by 120° can be provided for each ring 8. The rings 8 are stacked slightly offset in order to achieve good spatial coverage with carbon nanotubes.

Figure 4:
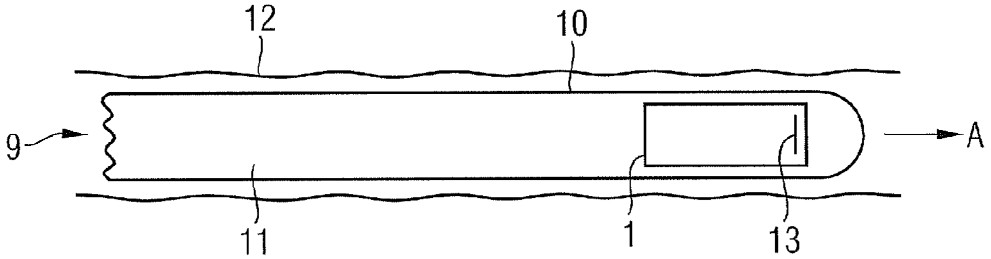
FIG. 4: a catheter with a miniature X-ray tube for emission in the radial direction
Figure 5:
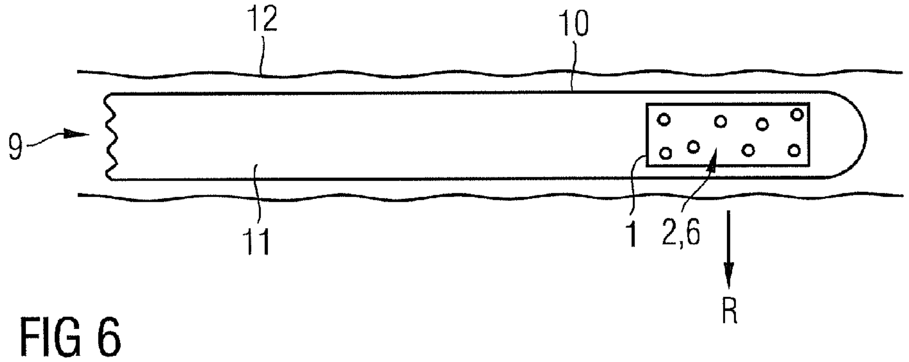
FIG. 5: a catheter with a miniature X-ray tube for emission in the axial direction
Figure 6:
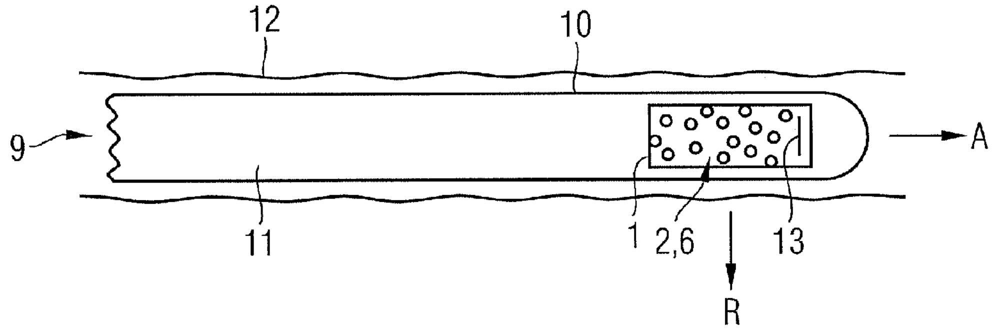
FIG. 6: a catheter with a miniature X-ray tube for emission in the axial and radial directions.

FIGS. 4 to 6 show different embodiments of a catheter 9 with a miniature X-ray tube 1 according to the invention in longitudinal section. The catheter 9 is introduced into a blood vessel 12. The miniature X-ray tube 1 is located in the distal end of the shaft 11 of the catheter 9. The miniature X-ray tube 1 is mounted within the biocompatible catheter sleeve 10. The necessary power supply lines and control elements are not shown. For reasons of clarity, no anode is shown.

FIG. 4 shows an embodiment of a miniature X-ray tube 1 with a second field emission cathode 13 with carbon nanotubes, which emits electrons in the axial direction A. This enables X-rays to be generated in the axial direction A.

FIG. 5 shows an embodiment of a miniature X-ray tube 1 with a first field emission cathode 2 with carbon nanotubes 6, which emits electrons in radial direction R. This enables X-rays to be generated in the radial direction R.

FIG. 6 shows an embodiment of a miniature X-ray tube 1 with a first field emission cathode 2 with carbon nanotubes 6 and with a second field emission cathode 13 with carbon nanotubes. Electrons are emitted in both the radial direction R and the axial direction A. This enables X-rays to be generated in the radial and axial directions R, A.

LIST OF REFERENCE NUMBERS

1 Miniature X-ray tube
2 First field emission cathode with carbon nanotubes 6
3 Anode
4 Cathode-focusing element
5 Housing section
6 Carbon nanotubes
7 Flexible carrier/film
8 Cylinder ring
9 Catheter
10 Catheter sleeve
11 Shaft
12 Blood vessel
13 Second field emission cathode with carbon nanotubes 6
A Axial direction of emission
L Longitudinal axis
R Radial direction of emission

The invention claimed is:

1. A miniature X-ray tube for an intravascular or an intracorporeal radiation treatment in a living being, comprising:
- a cylindrical housing with a longitudinal axis;
- a field emission cathode arranged in the housing; and
- a plurality of carbon nanotubes arranged on the field emission cathode that emit electrons,
- wherein the field emission cathode comprises a plurality of cylinder rings,
- wherein the carbon nanotubes are arranged on the cylinder rings, and
- wherein the cylinder rings are stacked in line and to offset the carbon nanotubes arranged on the cylinder rings.

2. The miniature X-ray tube as claimed in claim 1, wherein the field emission cathode is a cylindrical or cylindrical-tube-shaped first field emission cathode arranged in the housing concentrically about the longitudinal axis and the carbon nanotubes emit the electrons radially outward.

3. The miniature X-ray tube as claimed in claim 2, further comprising:
- a second field emission cathode arranged in the housing; and
- a plurality of further carbon nanotubes arranged on the second field emission cathode that emit further electrons in a direction of the longitudinal axis.

4. The miniature X-ray tube as claimed in claim 2, wherein the carbon nanotubes are arranged on an internal or an external side of the first field emission cathode.

5. The miniature X-ray tube as claimed in claim 2, wherein the first field emission cathode comprises a flexible carrier.

6. The miniature X-ray tube as claimed in claim 5, wherein the flexible carrier is a foil.

7. The miniature X-ray tube as claimed in claim 5, wherein the carbon nanotubes are printed or sputtered on the flexible carrier.

8. The miniature X-ray tube as claimed in claim 2, further comprising a cylindrical anode arranged in the housing symmetrically to the longitudinal axis outside the first field emission cathode.

9. The miniature X-ray tube as claimed in claim 1, wherein the carbon nanotubes emit the electrons in a direction of the longitudinal axis.

10. A catheter for an intravascular or an intracorporeal radiation treatment in a living being, comprising:
- a shaft; and
- a miniature X-ray tube arranged in a distal end of the shaft, wherein the miniature X-ray tube comprises:
  - a cylindrical housing with a longitudinal axis;
  - a field emission cathode arranged in the housing; and
  - a plurality of carbon nanotubes arranged on the field emission cathode that emit electrons,
- wherein the field emission cathode comprises a plurality of cylinder rings,
- wherein the carbon nanotubes are arranged on the cylinder rings, and
- wherein the cylinder rings are stacked in line and to offset the carbon nanotubes arranged on the cylinder rings.

11. The catheter as claimed in claim 10, wherein the field emission cathode is a cylindrical or cylindrical-tube-shaped first field emission cathode arranged in the housing concentrically about the longitudinal axis and the carbon nanotubes emit the electrons radially outward.

12. The catheter as claimed in claim 11, further comprising:

a second field emission cathode arranged in the housing; and a plurality of further carbon nanotubes arranged on the second field emission cathode that emit further electrons in a direction of the longitudinal axis.

13. The catheter as claimed in claim 11, wherein the carbon nanotubes are arranged on an internal or an external side of the first field emission cathode.

14. The catheter as claimed in claim 11, wherein the first field emission cathode comprises a flexible carrier.

15. The catheter as claimed in claim 14, wherein the flexible carrier is a foil.

16. The catheter as claimed in claim 14, wherein the carbon nanotubes are printed or sputtered on the flexible carrier.

17. The catheter as claimed in claim 11, further comprising a cylindrical anode arranged in the housing symmetrically to the longitudinal axis outside the first field emission cathode.

18. The catheter as claimed in claim 10, wherein the carbon nanotubes emit the electrons in a direction of the longitudinal axis.

* * * * *